(12) United States Patent
Tozian Cool

(10) Patent No.: US 9,839,105 B1
(45) Date of Patent: Dec. 5, 2017

(54) HEALTH STIMULATION DEVICES WITH VARIABLE LOW-VOLTAGE TUNERS AND OPTIONAL TEMPERATURE CONTROL

(71) Applicant: Cynthia A. Tozian Cool, Reading, MA (US)

(72) Inventor: Cynthia A. Tozian Cool, Reading, MA (US)

( * ) Notice: Subject to any disclaimer, the term of this patent is extended or adjusted under 35 U.S.C. 154(b) by 142 days.

(21) Appl. No.: 14/246,095

(22) Filed: Apr. 5, 2014

Related U.S. Application Data

(60) Provisional application No. 61/808,700, filed on Apr. 5, 2013.

(51) Int. Cl.
*H05F 3/02* (2006.01)
*A61N 1/32* (2006.01)
*A61N 1/14* (2006.01)

(52) U.S. Cl.
CPC ............... *H05F 3/02* (2013.01); *A61N 1/14* (2013.01); *A61N 1/32* (2013.01)

(58) Field of Classification Search
CPC ............... H05F 3/02; A61N 1/32; A61N 1/14
See application file for complete search history.

(56) References Cited

U.S. PATENT DOCUMENTS

| | | | | |
|---|---|---|---|---|
| 4,321,925 A * | 3/1982 | Hoborn | ................. | G01M 3/187 361/224 |
| 4,678,554 A * | 7/1987 | Oppitz | .................... | A01G 7/04 204/290.11 |
| 4,993,413 A * | 2/1991 | McLeod | ................. | A61N 2/02 600/13 |
| 5,014,699 A * | 5/1991 | Pollack | .................... | A61N 2/00 600/13 |
| 5,448,840 A * | 9/1995 | Cheskin | ................... | A43B 7/36 36/32 R |
| 5,527,259 A * | 6/1996 | Grace | ....................... | A61N 2/02 600/14 |
| 6,485,963 B1 * | 11/2002 | Wolf | ...................... | C12M 35/02 435/298.2 |
| 6,683,779 B2 * | 1/2004 | Ober | ........................ | A61N 1/14 361/212 |

(Continued)

FOREIGN PATENT DOCUMENTS

CA  2774833 A1 * 11/2013 ............... A61N 1/16

*Primary Examiner* — Scott Bauer

(57) ABSTRACT

The described devices, "grounded [ungrounded] stimulation devices" and "devices with [without] EMF removal", assist in maintaining and/or restoring bodily health primarily via two modes of operation:

In one set of embodiments, by reducing or removing the effects of electromagnetic fields (EMFs) encountered in daily life, through grounding.

In another set of embodiments, by stimulating and/or encouraging bodily healing processes through the supply of free electrons, at Schumann frequencies.

The embodiments function by allowing or increasing, respectively, the flow of low-current, low-voltage current into or out of the body, at levels safe for humans and animals, through conductive materials in electrical contact with the body. These devices use conductive materials incorporated into and/or comprising handheld, wearable or other items that directly contact the body, including shavers, clothing, shoes, mousepads, footstools, bedding, jewelry and collars. Certain devices allow the addition of heat/cold.

10 Claims, 9 Drawing Sheets

(56) References Cited

U.S. PATENT DOCUMENTS

| | | | | |
|---|---|---|---|---|
| 6,684,107 B1* | 1/2004 | Binder | A61N 1/32 | 607/145 |
| 7,212,392 B2* | 5/2007 | Walker | H05F 3/025 | 361/212 |
| 7,349,194 B2* | 3/2008 | Elliott | A61N 1/14 | 361/220 |
| 7,609,503 B2* | 10/2009 | Hee | A61N 1/14 | 361/212 |
| 7,724,491 B2* | 5/2010 | Ober | A61N 1/14 | 361/220 |
| 8,405,377 B2* | 3/2013 | Yu | G05F 3/262 | 323/315 |
| 8,825,174 B2* | 9/2014 | Panting | A61N 1/0484 | 600/386 |
| 2002/0002388 A1* | 1/2002 | Mann | A61H 39/002 | 607/2 |
| 2004/0254624 A1* | 12/2004 | Johnson | A61N 1/0452 | 607/149 |
| 2005/0187497 A1* | 8/2005 | Nguyen | A61N 1/32 | 601/21 |
| 2008/0249587 A1* | 10/2008 | Cho | A61H 39/002 | 607/46 |
| 2010/0324611 A1* | 12/2010 | Deming | A43B 3/0005 | 607/2 |
| 2011/0105827 A1* | 5/2011 | Hesse | A61F 5/0003 | 600/14 |

* cited by examiner $$t_{FOUT}(s) = 8^{FDIV2:0} \times RSET / 1.08E11$$

FIG. 1

| FDIV2:0 | $t_{(FOUT)}(s)$ | FOUT (Hz) |
|---|---|---|
| 000 | 3.3µ – 111.1µs | 300k – 9k |
| 001 | 26.4µ – 888.88µs | 37.5k – 1.125k |
| 010 | 211.2µ – 7.11ms | 4.69k – 140.62k |
| 011 | 1.7ms – 56.88ms | 586 – 17.578 |
| 100 | 13.6ms – 455.16ms | 73.25 – 2.197 |
| 101 | 108.8ms – 3.64 | 9.16 – 0.2746 |
| 110 | 870.4ms – 29.15 | 1.14 – 0.0343 |
| 111 | 6.99 – 29.15 | 0.143 – 0.00429 |

FIG. 1A

HEALTH STIMULATION DEVICES WITH VARIABLE LOW-VOLTAGE TUNERS AND OPTIONAL TEMPERATURE CONTROL

CROSS-REFERENCE TO RELATED APPLICATION

Provisional Patent Application No. 61,808,700, filed Apr. 5, 2013, titled "Health Stimulation Devices with Low-Voltage Tuners and Optional Temperature Control".

BACKGROUND OF THE INVENTION

The purpose of the described inventions is to reduce and possibly reverse the deleterious effects of electromagnetic field (EMF) interactions on the human and animal body and on plants.

From sources including cellular phones, PCs and tablets, to ordinary house wiring through high-tension power transmission lines, people in the developed world and, increasingly, in the developing world, are exposed to numerous occasional through near-constant sources of EMF emissions [1, 2, 3].

Many reports, based on research spanning at least the last 50 years, have suggested a causal link between electromagnetic field (EMF) exposure and newly described conditions, including (especially) electromagnetic hypersensitivity [4, 5]. Researchers have noted that increasing EMF exposure correlates with the increased incidence of numerous health conditions, such as acquired immune deficiency syndrome (AIDS), sudden infant death syndrome (SIDS), cancer, birth defects, depression, learning disabilities, Parkinson's disease, Alzheimer's disease, chronic fatigue syndrome (CFS) [4], and other conditions and diseases, including some of unknown etiology. Many now attribute these correlations to cause-and-effect relationships, which may be further complicated by other factors such as environmental toxicity, nutritional deficiencies and side effects from medications [6, 7, 8, 9, 10, 11, 12, 13, 14, 15, 16].

Scientific studies on EMF exposure indicate that various forms of electrotherapy are emerging as protective and/or preventive techniques—methods using and even augmenting human and animal bodies' own electrical systems to stimulate healing [17, 18, 19, 20, 21].

This patent application claims, in part, inventions relating to the generation and application to a body of a Schumann resonance of 7.83+/−0.5 Hz, in the form of a square wave electrical signal, in the preferred embodiment. Physicist Winfried Otto Schumann predicted Schumann resonance in 1952. The 7.83 Hz Schumann resonance peak is the primary naturally occurring electromagnetic wave within the cavity between the earth's surface and the conductive ionosphere, which extends from approximately 50 miles to 600 miles above the earth's surface. Schumann resonances occur naturally as standing waves within this cavity, which acts as a closed waveguide. However, scientists have determined that naturally occurring Schumann resonance frequencies, with which all living things evolved, and which may be necessary to their health, have become immeasurable, due primarily to the interference from ubiquitous sources of man-made EMFs [22].

EMF interference with the natural Schumann resonance in the environment has been demonstrated to have a significant measurable effect on mental and physical health [23]. In 1963 Rutger Wever, of the Max Planck institute, constructed an underground bunker to examine the effects on human subjects of circadian rhythms, which regulate our diurnal cycle. For thirty years Dr. Wever studied young, healthy student volunteers living in the bunker for weeks at a time, being completely shielded from the extremely low frequency (ELF) aboveground natural resonances. He reported that during their stay, subjects started to have headaches and began feeling sick, and that their circadian rhythms were completely out of sync with the natural circadian rhythm of 24.1-24.2 hours. In the experiment, Dr. Wever then secretly introduced the 7.83 Hz frequency into the bunker environment using a magnetic pulse generator, and reported witnessing a decrease or disappearance of the headaches, stress and other issues, and that subjects' sense of well-being was restored [23, 24].

Nobel prize-winning scientist Dr. Luc Montagnier studied DNA in water. He discovered that bacterial DNA emitted measurable low frequency electromagnetic waves. In his experiments, Dr. Montagnier completely filtered the DNA from the water. He then introduced Schumann resonance, and nucleotides organized into DNA. In the absence of Schumann resonance of 7.83 Hz, DNA did not appear [24, 25, 26].

Furthermore, scientific studies have demonstrated that EMF interference from 50 Hz and 60 Hz electric or magnetic fields from electric blankets has a measurable effect on the pineal gland and diminishes melatonin production in humans [4, 26]. Melatonin is a powerful natural antioxidant, and the lack of melatonin production may have significant biological consequences, including (particularly) possible carcinogenesis in humans. Melatonin is a free radical scavenger that assists the body in counteracting free radical damage by donating electrons to neutralize them.

BRIEF SUMMARY OF INVENTION

The described devices include two types of health stimulation devices; first, those that are electrically grounded, and second, those that are ungrounded.

The electrically grounded stimulation devices will allow a flow of free electrons both into and out of the body, while the ungrounded stimulation devices will allow a flow of free electrons into the body. Both will counteract (to reduce or substantially eliminate) the interaction with the body of manmade electromagnetic radiation from various sources encountered in daily life. Both grounded and ungrounded stimulation devices will supply a low-voltage flow of free electrons into the body in order to reduce or eliminate free radical damage. A variable flow of low-voltage free electrons will provide a safe and beneficial electrical source to the surface and interior of the body. Temperature control (heating or cooling), when provided and used with certain of the described electrical devices, will assist in reducing tension and relieving bodily discomfort or pain.

The described devices will incorporate electrically conductive materials such as threads, metals, semiprecious stones, fibers and leather, either woven into, attached to and/or shaped, as appropriate, into fabrics for clothing or into practical devices or adornments for everyday use. A single grounded device may be used either alone or in combination with an ungrounded device to reduce the effects of EMF interactions on the body.

BRIEF DESCRIPTION OF THE DRAWINGS

FIG. 1 is the fixed frequency output (FOUT) calculation equation, where FDIV2:0=0 to 7.

FIG. 1A is a table of FOUT per FDIV2:0 combination.

DETAILED DESCRIPTION OF INVENTION

Figure 2:
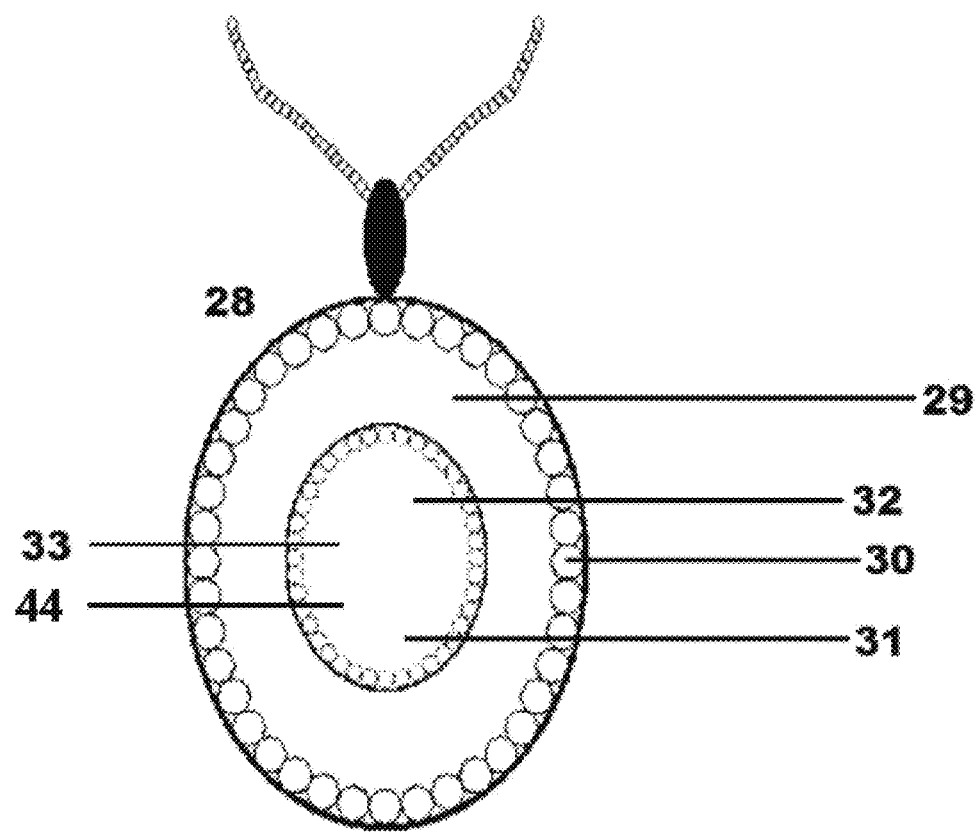
FIG. 2 is an illustration of an electrically conductive pendant made of piezoelectric quartz, sterling silver, copper, gold or another electrically conductive metal and Schumann resonance generating and timing circuit powered by a 2-volt battery hidden within a hollow compartment contained within the pendant.

All references to the body herein apply to both humans and animals, including but not limited to pets (e.g., cats, dogs), working animals (e.g., rescue dogs, guide dogs, race horses, draft horses) and captive animals (e.g., zoo animals, laboratory test animals), and in certain circumstances apply to plants.

This invention is multifaceted, incorporating a user-controlled low-voltage power supply to produce pulsed current in many of the contemplated devices. These devices are useful in the home, the workplace, or outdoors—wherever EMF exposure is present. Some devices may be used individually, while others combine in any way that will supply the low-voltage pulsed current indirectly through multiple electrically conductive surfaces, at least one of which is in contact with the body (e.g., as a series). The devices may be in continuous electrical contact with the body or plant, or may be in intermittent or occasional electrical contact, and the devices may function or be used continuously, intermittently or occasionally. The devices that will not include a self-contained power source will, nonetheless, require a source of electrical current in order to provide a source of free electrons to the body. This is achieved by one or more electrically conductive items in contact with the body (e.g., clothing, chair arm, mousepad), in conjunction with one or more other electrically conductive items that supply electrical energy.

Examples of devices that may be used alone include, but are not limited to, electrically grounded conductive shoes with pulsed low-voltage current that allow an electrical connection from the wearer's skin through the conductive sole or heel, which is in intermittent contact with the grounded conductive walking surface, or an electrically conductive footstool providing a low-voltage pulsed current source through contact with bare feet or electrically conductive hosiery, or through an electrically conductive stake inserted into the potting soil of a houseplant. Examples of devices that operate through an indirect source of low-voltage current to eliminate or reduce the effects of EMF interactions include but are not limited to a sweater with electrically conductive yarns or a shirt with electrically conductive threads, where the devices do not contain a low-voltage current supply. These items require a supply of current through electrical contact with an electrically conductive item containing and providing a low-voltage current, including but not limited to a metal pocketbook, necklace, belt or device specifically provided for the purpose of providing power.

Protecting the body from EMF may be done in two ways: using devices separately, or using devices in combination.

Protecting the body, using devices separately: The first way to protect the body from EMF damage is to use the body itself as an electrically conductive device that is effectively a Faraday cage. The electrical ground supplies a method of counteracting the effects of EMF on tissue, by providing free electron flow through the body, which itself is a natural conductor. Electrical grounding removes or reduces most of the EMF interacting with the body. The grounding of the devices could be via an electrically conductive connection (using a wire with an alligator clip on each end, for example) to a metal object providing an electrical sink (e.g., plumbing, where building codes require plumbing to be grounded), or through a properly grounded electrical outlet, or via an article of clothing, or by other means.

Another way to protect the body separately from EMF damage is to induce a pulsed flow of free electrons through the body via the application of Schumann resonance [23, 24, 25]. Free electrons, which are negatively charged, counteract free radicals, which are positively charged electrical forces within the body. Free radicals are also reduced, for example, by melatonin, a powerful antioxidant produced in the body [4, 25]; however, melatonin production is inhibited by prolonged exposure to environmental EMFs. According to certain of the described inventions, the flow of electrons would be directed into the body to counteract the production of positively charged free radicals produced in the body. Free radicals are electron scavengers that create damage within the body by damaging cells. Electrons would thus act as powerful antioxidants to neutralize free radicals, by donating electrons that neutralize them, especially in the absence of sufficient melatonin [4, 25]. Direct delivery to the body of pulses of free flowing electrons at a natural Schumann resonance using electrically conductive materials in contact with the body will counteract the inhibition of natural Schumann waves by manmade EMFs.

In order to reduce free radical damage, a device with a variable low-voltage source, including but not limited to an electrically conductive mat or mousepad, could be used alone. This device would be in electrical contact with the body and would provide an instantaneous flow of free electrons to neutralize the positively charged areas of the body. The body contains an elaborate electrical network, the nervous system, and generates and utilizes electrical signals that must meet certain requirements for the proper functioning of cells and the body as a whole. Cells in the body require negative charge to function properly; each cell requires a variable −20 to −50 millivolts of electricity to survive or to make a new cell [19]. However, sometimes the body can exhibit areas of measurably improper voltage (for example, from positively charged to −20 mV), and it is believed that these improper voltages signify health problems [19], such that changing the prevailing charge back to or toward the −20 to −50 mV range may encourage improved cellular function.

Protecting the body, using devices in combination: Grounding devices and Schumann resonance circuitry may be used together to protect the body from EMF damage. By combining the two modalities, the user has a choice of using the device either for grounding or for Schumann resonance pulsing. Application of the Schumann resonance on one area of the body, while grounding another, would combine the action of the two modes, further improving EMF protection. It is possible that the weak Schumann resonance pulse, if applied to the same body part and at the same instant as grounding, could cause the pulsing action to be discharged to ground potential, negating its benefits. Shoes, for example, are often not on the ground at the same time and are sometimes simultaneously off of the ground, and so both grounding and resonance circuitry may be used concurrently.

Of significance are the meridians that run through the body along specific routes along the back, torso, arms, face, head, hands and feet [19]. These meridians have distinct measurable voltages in a healthy body, and measurements of these voltages at certain points on the surface of the skin indicate which areas of the body have improper voltage, which can indicate problems in bodily functioning, or even a disease [19]. It is along these meridians or in these areas where additional current flow(s) could be of great benefit. Therefore, shirts with electrically conductive threads along the meridians of the back, for example, might be beneficial in helping the body heal from one or more injuries or particular diseases in proximity to these meridians.

The user is able to enable and disable the flow of current through electrically conductive surfaces in electrical contact with the body by turning on or off, independently, the grounding or the pulsed current at the preferred rate of 7.83 Hz in the preferred embodiment. Power may be supplied by a low-voltage battery, as well as (and as a safer or more convenient alternative to) a power converter connected to an AC electrical source (household, office, etc.), or by another conversion means, such as a 12 VDC-to-2 VDC converter in an automobile.

A heat source may be incorporated into or used with some of the described devices to warm the feet or other body part(s). A source of cold may also be incorporated into or used. These heating/cooling devices would be used in combination with an electrically conductive item such as a knee wrap or leg wrap, over an electrically conductive cold pack, for example, to supply and direct the flow of free electrons to the site of injury and/or discomfort and promote healing and/or analgesia. A heat source may be built into a grounded footstool that supplies a flow of free electrons, as another example.

It has been demonstrated that the addition of an extremely low frequency (ELF) manmade alternating current (AC) upregulates insulin-like growth factor-binding protein 3 (IGFBP3) [21]. Insulin-like growth factors induce the growth of healthy cells. However, they may also promote the growth of cancerous lesions and conditions such as acromegaly and premature aging [11, 12, 13, 14, 15, 16, 17, 18, 19, 20, 21]. Treatment using alternating currents (ACs) may be a suitable choice for some conditions or diseases, but is not a suitable choice in the preferred embodiments.

The human body is considered to be mechanistic by modern medicine, but is actually quantum mechanical, and exhibits natural resonant frequencies of around 10 Hz, an example being natural alpha brain waves. Atmospheric Schumann resonance, measured at 7.83+/−0.5 Hz including seasonal variations, exposes the body to one of the earth's resonant frequencies with which all living beings have evolved, and is quite close to 10 Hz, one of the body's natural resonant frequencies. However, Schumann resonance is thought to be periodically absent from the atmosphere naturally, but most importantly, it may be overwhelmed (drowned out) by ubiquitous man-made environmental EMFs [22]. Schumann resonance, a weak, naturally occurring electromagnetic field existing in the earth's atmosphere in the cavity between the earth's surface and the beginning of the ionosphere is today virtually indistinguishable from background electromagnetic radiation fields due to the presence and interference of the stronger and ubiquitous man-made EMFs, especially those from the harmonics of 50 and 60 Hz AC power lines in homes and buildings and outside in urban areas [22], of high-voltage three-phase alternating current (AC) transmission lines, of transformers, and from wireless communication towers, for example.

In the preferred embodiment, devices may be engineered from readily available manufactured materials or from products specifically designed for electrostatic discharge (ESD), including but not limited to electrically conductive carbon fiber cloth, ESD shoe straps, ESD rubber mats, ESD anti-static grounding cords, ESD grounding shoes, electrically conductive fabrics such as polyester or carbon fiber; cotton containing stainless steel, carbon fiber, silver 30 or copper wire; and far infrared carbon heating wire for heat generation. General-purpose plastics such as nylon, polyvinylchloride (PVC), polyethylene (PE), and/or gel may be incorporated into the manufacturing of cold and hot packs. Insulating materials such as rubber may be incorporated. The electrical conductivity of materials including leather, piezoelectric crystals and/or other piezoelectric materials 29, silver 30, gold, stainless steel, copper and alloys will be adequate to address the utility and design requirements of devices that will be formed/incorporated into jewelry, practical items (e.g., belts and belt buckles) and decorative items (e.g., adornments such as embroidery). Other electrically conductive materials that are suitable alternatives to any of the aforementioned materials, may also be incorporated in and/or replace the materials in the embodiments.

A CMOS TS3004 integrated circuit (IC) 31 timer is contemplated for use in the preferred embodiment for the pulsed circuit. The TS3004 IC 31 requires a single external resistor of 3.367 M-Ohms 40 to meet the criterion of Schumann resonance of 7.83 Hz. Other integrated circuits such as the 555 series are also suitable for this embodiment to obtain any one or more of the natural Schumann resonance peaks of 7.83, 14.3, 20.8, 27.3 and 33.8 Hz. Other values of resistors or the use of surface potentiometers are contemplated to control the supply of Schumann resonance, due to the inherent internal sensitivities and uncertainties in the output of each device. The preferred embodiments contemplate resistance values other than those used to generate 7.83 Hz, and contemplate adding other pulses or other naturally occurring Schumann resonances. In addition, the application of a DC low-voltage power supply, i.e. direct current, is being contemplated in this embodiment as an alternative to pulsing.

The TS3004 integrated circuit 31 has an internal configuration and settings that enable the preset frequency of the timer according to instructions in its documentation [27]. The output frequency (FOUT) of the timer is determined by solving equation 1 [FIG. 1] and setting the internal logic for frequency divider input FDIV2:0 to 100, corresponding to a value of 4 into the equation, as shown in Table 1 [FIG. 1A]. This determines an FOUT programming resistor input (RSET) value of 3.367 M-Ohms 40. The operating voltage requirement of the TS3004 IC device 31 is between 1.55 V and 5.25 V, which enables use of a weak supply current in microamperes and a weak flow of electrons, simulating earth's natural Schumann wave characteristics. The preferred embodiments allow the selection of any voltage between 1.55-5.25 V (or in the range permitted by an alternative to the TS3004 integrated circuit 31) on each device and allow the flexibility to change the voltage at any time. Various materials have differing conductivities, and this would have an effect on the current and voltage supplied to the body, while the frequency would remain as designed for the circuit.

The generation of a square wave is a satisfactory approximation to the natural Schumann resonance wave, which is a standing wave produced between the earth and the electrically conductive and positively charged ionosphere, which occupies a region extending from approximately 50 miles to 600 miles above the surface of the earth. Schumann resonance wave amplitudes, by comparison to the size of a person, are thus extremely large, allowing the earth's natural Schumann wave to appear as a square wave over the surface of the body. Thus, the use of a square wave generator is satisfactory to produce a Schumann-like wave on the surface of the body. The use of the SC3004 integrated circuit 31 may simplify the circuit logic and reduce the component requirements and cost.

Other consumer devices being contemplated for the preferred embodiment would include portable Schumann resonance pulse generating devices for use in places such as the home or car and with items such as cell phones. These devices would be constructed of the same above-mentioned electrically conductive materials and the Schumann resonance circuitry described herein, and would operate by generating a flow of free electrons on the electrically conductive surface of a material/item (or multiple such materials/items in series) that is (are) in contact with the surface of the body. Such devices could be hand-held, such as a car steering wheel cover or a self-adhesive or self-attaching flexible pad for use with handheld EMF-generating devices such as cordless phones and hairdryers. Various contemplated devices may attach to a showerhead or a water faucet or be incorporated into a shower mat to deliver Schumann resonance through bodily contact and/or through flowing/standing water. The preferred embodiment could apply the same type of technology through direct contact with free-electron generating electrically conductive materials and the surface of the body, with broad application in or with the various consumer devices under consideration.

Grounding devices for electrostatic discharge have been available for many years. The described inventions use certain devices to ground the body, as in a grounded Faraday cage, and as Schumann resonance devices through the generation of free-flowing electrons, with a safe current, through electrically conductive materials in electrical contact with the body. The grounding being considered in the preferred embodiment could be via simple alligator clips and copper wire leads connecting the device to the ground potential. Other means contemplated in the design for obtaining ground potential in this embodiment include: grounding via an electrical connection to a grounding rod inserted into the earth, instead of using the alligator clip connecting the device to ground potential; the use of a snap-on or other connector (e.g., for connection to a plumbing pipe); and the addition of a surge protection device such as a resistor or a fuse, for the protection of the user and devices from power surges. The preferred embodiment does not limit the utilization of methods enabling safe grounding or to add a heater/cooler to an invention or the use of an AC-to-DC converter (to avoid the typical 50 or 60 Hz AC EMF emissions).

The devices described will assist the body in healing, by helping to restore the body's homeostasis by removing, to the extent possible, the effects of EMF exposure and free radical damage before irreversible damage has occurred, and/or by exposing the skin and body to electrical charges at the earth's diminished Schumann resonance frequency. Direct application of Schumann resonance to the surface of the body would help to counteract the problems caused by the presence and interaction of manmade EMFs before it penetrates into the body.

Figure 3:
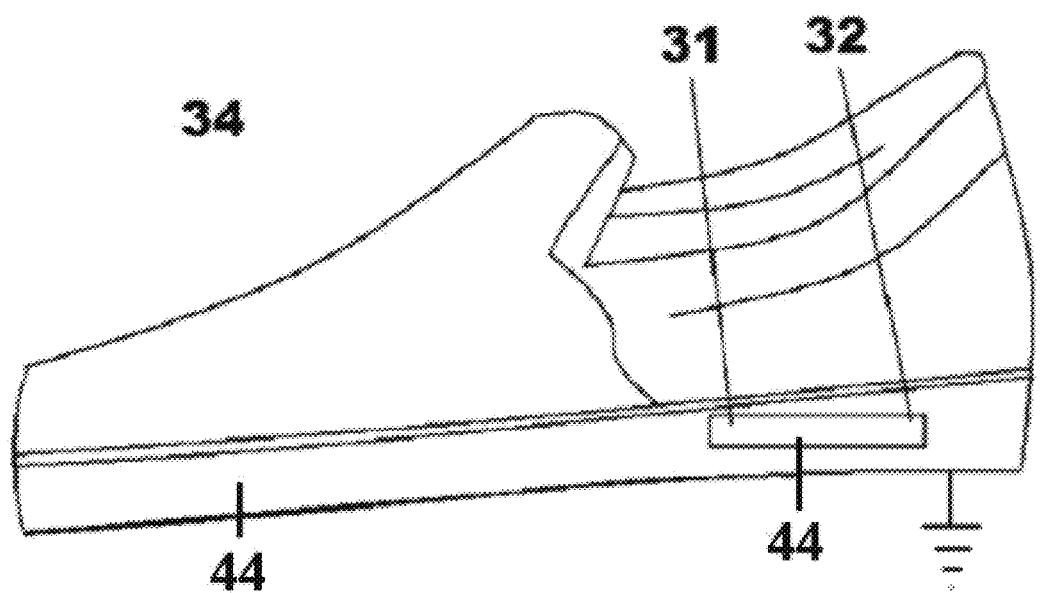
FIG. 3 is an illustration of a grounded electrically conductive shoe containing the Schumann resonance generating and timing circuit, powered by a 2-volt battery.
Figure 4:
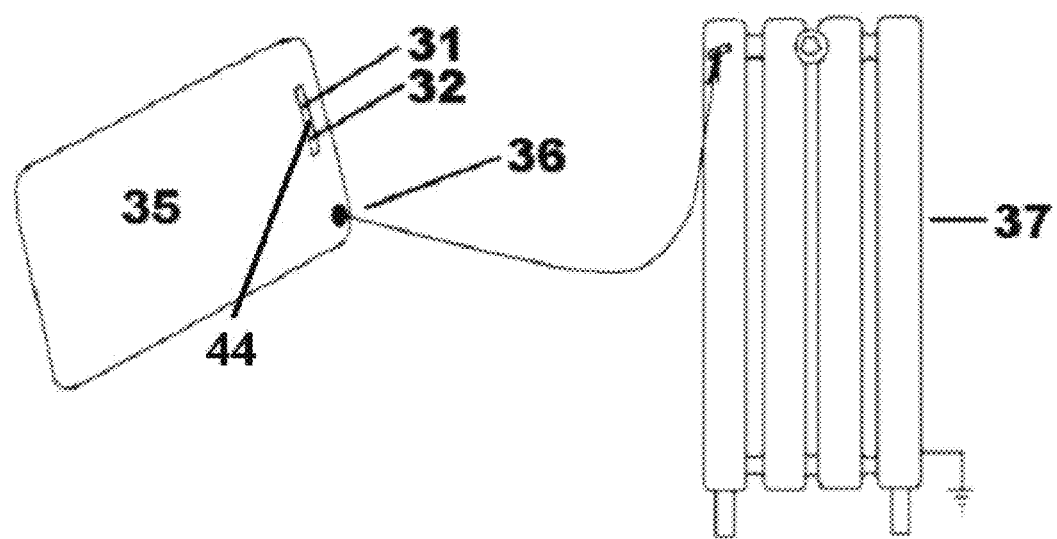
FIG. 4 is an illustration of an electrically conductive computer mousepad containing the Schumann resonance generating and timing circuit powered by a 2-volt battery. The mousepad is illustrated connected to an antistatic grounding cord and grounded to a household radiator.
Figure 5:
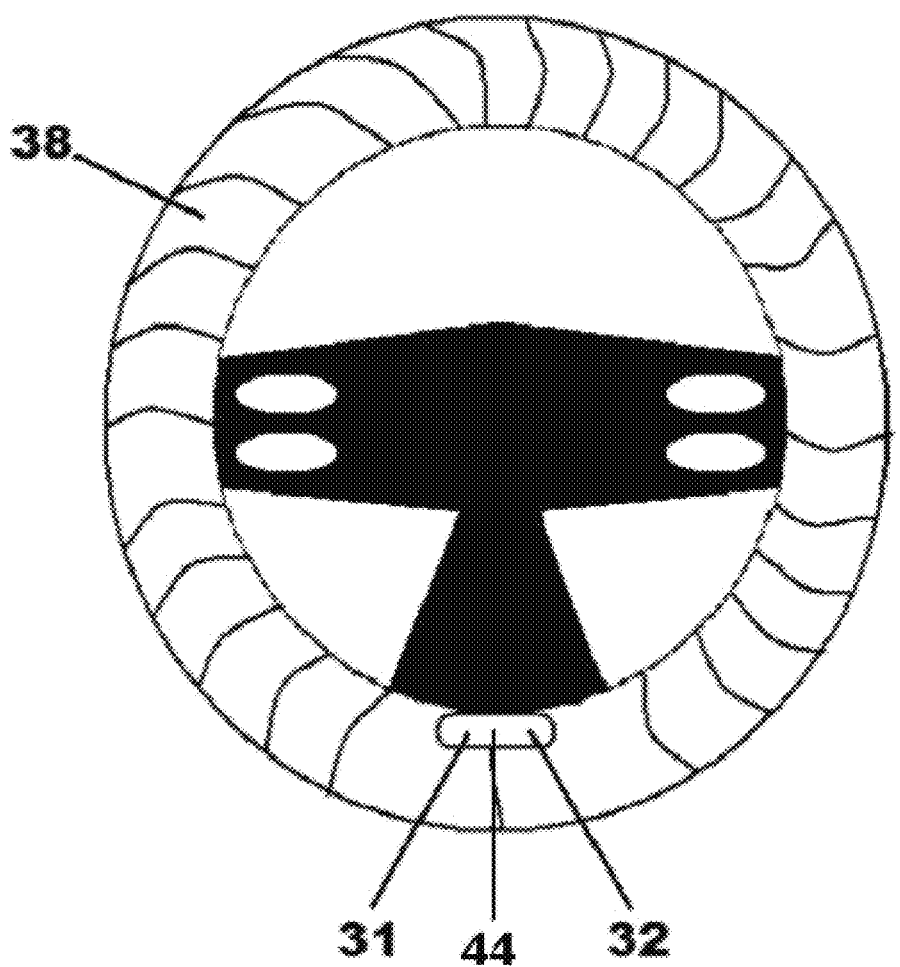
FIG. 5 is an illustration of an electrically conductive steering wheel cover containing the Schumann resonance generating and timing circuit powered by a 2-volt battery.
Figure 6:
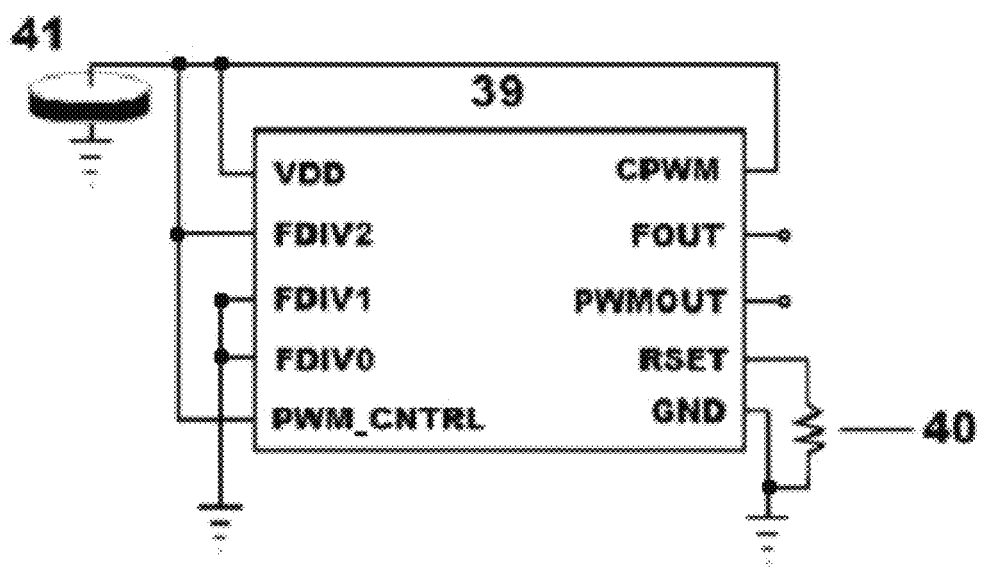
FIG. 6 is the TS3004 integrated circuit diagram with an external 3.367 M-Ohm resistor and button cell battery.
Figure 7:
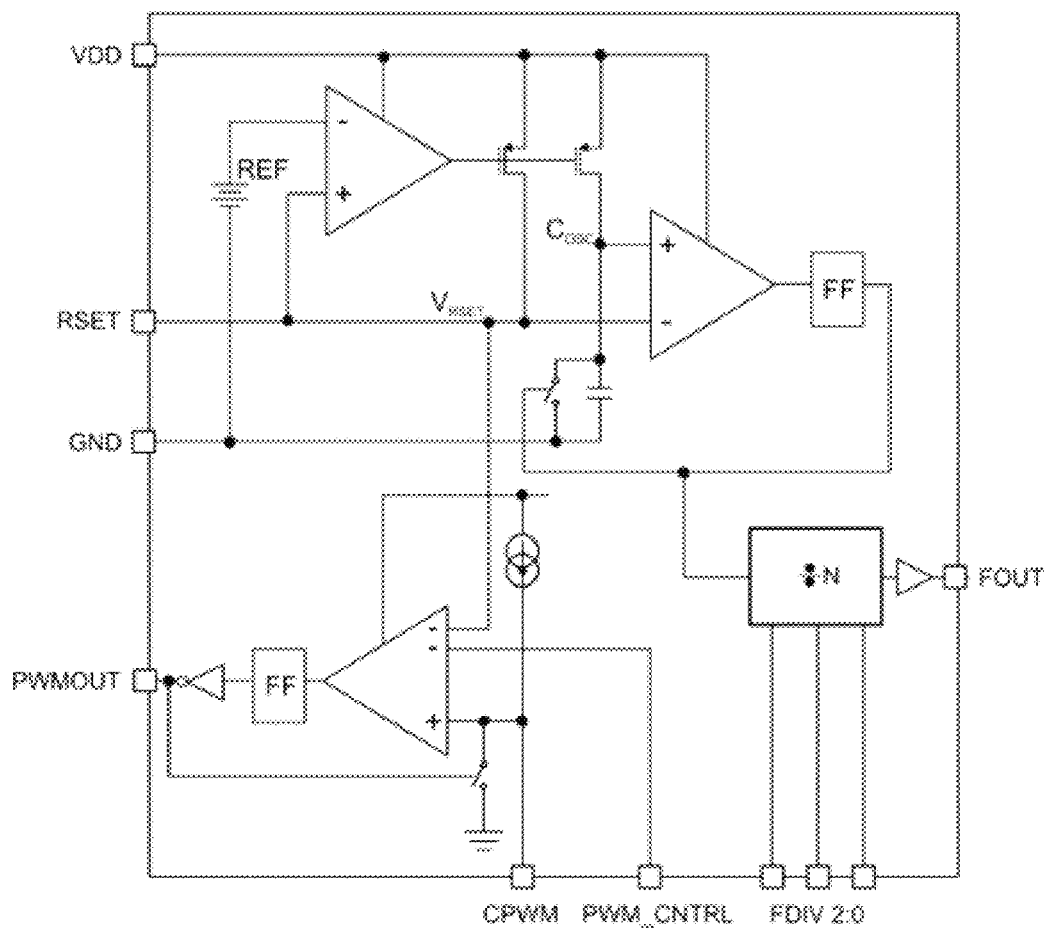
FIG. 7 is a block diagram of the TS3004 integrated circuit.
Figure 8:
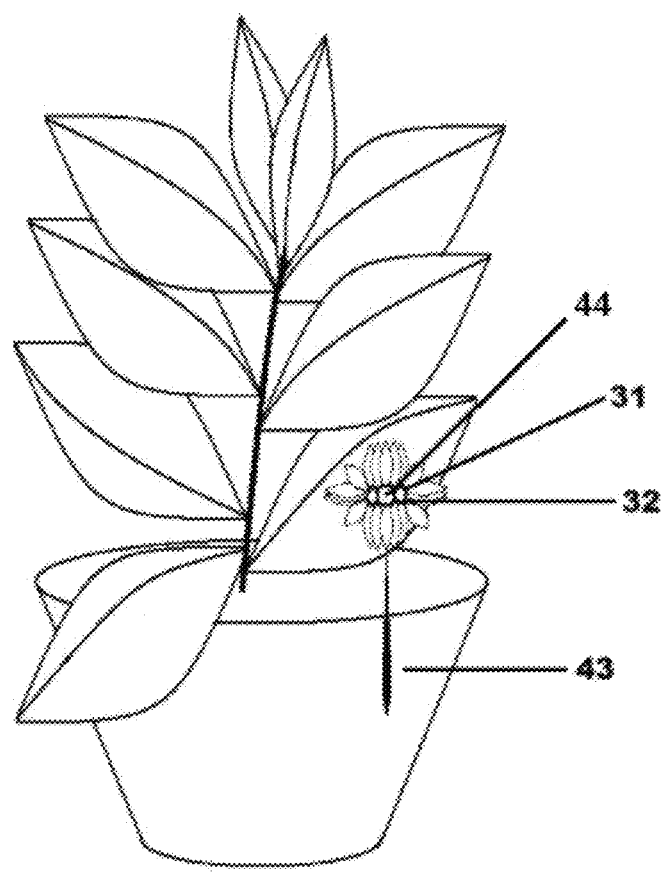
FIG. 8 is an illustration of a Schumann resonance generating and timing circuit, powered by a 2-volt battery, on an electrically conductive metal stake that is inserted into the soil of a houseplant.
Figure 9:
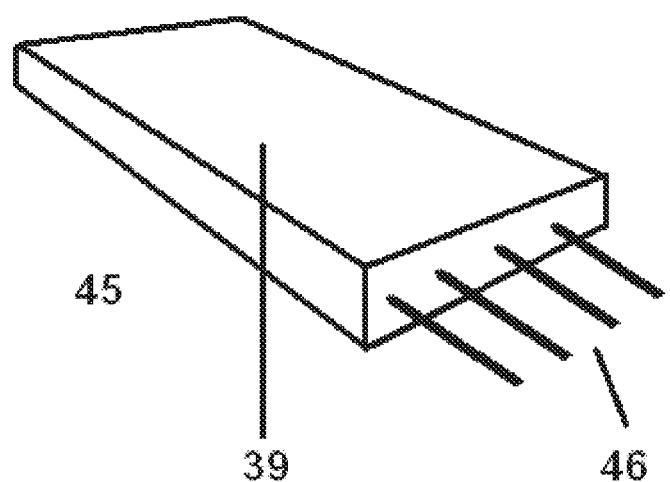
FIG. 9 is an illustration of an enclosure for the circuit and other components.

Diagrams illustrating the preferred embodiment include the following descriptive example applications. FIG. 2 illustrates an electrically conductive pendant 28 with quartz piezoelectric crystals 29 made of highly conductive sterling silver 30. The pendant contains the Schumann resonance generating timing circuit 31 with a 2-volt battery power supply 32 to generate the resonance frequency of 7.83 Hz with power switch 44 within a hollow compartment contained within the pendant 33. FIG. 3 illustrates a grounded electrically conductive shoe 34 with power switch, 44 a 2-volt battery supply 32, Schumann resonance generating timing circuit 31 with power switch 44. FIG. 4 illustrates a grounded mousepad made of an electrically conductive rubber mat 35, a Schumann resonance generating timing circuit 31 and a 2-volt battery power supply 32 with power switch 44 connected to an antistatic grounding cord with snap and alligator connectors 36 and to a household radiator 37. FIG. 5 illustrates an electrically conductive rubber steering wheel cover 38 containing the Schumann resonance generating timing circuit 31, a 2-volt battery supply 32 and power switch 44. FIG. 6 is the TS3004 timing circuit diagram 39 with an external 3.367 M-Ohm resistor 40 to generate a Schumann frequency of 7.83 Hz and showing a button cell battery 41. (See Touchstone document [27] for further details.) FIG. 7 is a block diagram of the TS3004 circuit 42. (See Touchstone document [27] for further details.) FIG. 8 is a device with an electrically conductive stake made of copper 43, holding Schumann resonance generating timing circuit 31, 2-volt battery supply 32 and power switch 44 with the stake inserted into the soil of an indoor houseplant. FIG. 9 illustrates an enclosure 45 for the circuit 39 and, when required, internal power source (e.g., battery 41); leads 46 to/from the circuit 39 introduce power from an external source when required, supply the signal from the circuit 39 to an outside recipient, provide grounding if necessary, and allow on/off control; the enclosure 45 is fabricated from electrically insulating and conductive materials.

The invention claimed is:
1. A device comprising:
an electronic integrated pulse generating and timing circuit,
a power source,
a power switch and
a settings switch,
wherein the device is enclosed by electrically insulating and electrically conductive materials,
wherein the device provides to the conductive body of a person, planting medium, or animal, pulsed free electrons with Schumann resonance frequency of 7.83+/−0.5 Hz via a portion of the electrically conductive material which is in contact with the conductive body,
wherein the device operates in:

a first grounded mode which causes the pulsed free electrons to flow into and out of the conductive body, and a second ungrounded mode which causes to free electrons to flow into the conductive body, wherein the settings switch causes the device to operate in four different states; a first state which causes the device to operate in the ungrounded mode; a second state which causes the device to operate in the grounded mode; a third state which causes the device to operate in both the grounded and the ungrounded modes simultaneously; and a fourth state which places the switch in an off position;

wherein the source of power for the circuit comprises at least one of the following:

a DC battery, an AC-to-DC converter, a DC-to-DC converter, a solar cell or a piezoelectric crystal, and wherein the power provided by the power source is below the potential that would cause pain, discomfort or injury to the conductive body or damage to the device.

2. The device of claim 1, wherein the device is in contact with or electrically connected to an electrically conductive pad or a grounding mat, computer mousepad, pad/covering for a footstool/seat/bed, yoga/exercise mat, mat for an animal habitat, vehicle steering wheel, or other decorative or utilitarian item or portion of such an item which is made of flexible conductive rubber and/or other conductive fabric and/or materials-comprising at least one of the following; leather, stainless steel, silver, gold, copper, and/or fabric with electrically conductive threads in direct contact with the body.

3. The device of claim 1, wherein the device is incorporated into, onto or attached to an electrically conductive stake, where the device and the stake are comprised of insulating and electrically conductive materials comprising at least one of the following; plastic, rubber, metal foil, metals such as copper, silver or stainless steel, or piezoelectric materials in contact with the conductive potting soil holding one or more plants.

4. The device of claim 1, wherein the device is incorporated into an item comprising at least one of the following; a knee wrap or neck support, that may include a bag or other container containing a solid, gel or liquid coolant or heating material, where such item comprises insulating and electrically conductive materials comprising at least one of the following; plastic, rubber, metals, foil, piezoelectric material and fabric with conductive threads in direct contact with the conductive body of a person or animal.

5. The device of claim 1, wherein the device is in electrical contact with moving or standing water entering, passing through or contained within a water pipe/faucet, shower head, bathtub, shower stall, footbath or water bowl, where the water is in electrical contact with the conductive body of a person or animal.

6. The device of claim 1, wherein the device is in electrical contact with an electrically conductive item comprising at least one of the following; a water pipe/faucet, shower head, bathtub, shower stall, footbath, water bowl, shower mat, or bath mat, or other item used in a shower or bath, comprising electrically insulating and conductive materials comprising at least one of the following; stainless steel, silver, copper, plastic, and/or rubber, where said item comes into electrical contact with the conductive body of a person or animal.

7. The device of claim 1, wherein the device is incorporated into or in electrical contact with an item comprising at least one of; an electrically conductive water pipe/faucet, shower head, bathtub, shower stall, footbath, shower mat, or bath mat, or other item used in a shower or bath, or a water bowl, comprising electrically insulating and conductive materials comprising at least one of the following; stainless steel, silver, copper, plastic and/or rubber that is in electrical contact with water that is in electrical contact with the conductive body of a person or animal.

8. The device of claim 1, wherein the device is incorporated into an item comprising at least one of the following; a pair of shoes, article of clothing, animal collar/harness/lead, jewelry, belt or handbag, comprising electrically insulating and conductive metals comprising at least one of the following; stainless steel, gold, silver, or copper, or rubber, plastic, piezoelectric material, and/or fabric with conductive threads, where operation of the device may be activated in each conductive item, and the intermittent and/or alternating contact with the conductive body permits the devices to be operated separately, independently or simultaneously in grounded and/or ungrounded modes.

9. The device of claim 1, wherein the device is a self-adhering or self-attaching item comprising electrically insulating and conductive material comprising at least one of the following; leather, rubber, plastic, stainless steel, copper, or fabric with conductive threads, that is in contact with an item comprising at least one of the following; vehicle steering wheel, steering wheel cover, hairdryer, cordless or cellular phone, or computer keyboard cover in direct contact with the conductive body of a person.

10. The device of claim 1, wherein the device is a mat, vehicle seat or seat cover, mousepad, computer keyboard cover, pad/covering for a footstool/seat/bed, yoga/exercise mat, mat for an animal habitat, which is made of flexible conductive rubber and/or other conductive fabric and/or materials comprising at least one of the following; leather, stainless steel, silver, gold, copper, one or more piezoelectric materials, and/or fabric with electrically conductive threads in direct contact with the body and conductively connected to an electrical ground comprising one of the following; conductive grounding rod, an ESD antistatic grounding strap, a conductive cord with one AC ground pin or snap and/or alligator clip connectors to connect and/or disconnect to ground potential through grounded household pipes or a grounded AC outlet.

* * * * *